United States Patent

Mauz et al.

[11] 3,969,530
[45] July 13, 1976

[54] 4-HYDROXY-3,5-DI-ALKYL-PHENYL-PROPIONIC ACID COMPOSITION SUITABLE AS LIPID LOWERING AND ANTI-DIABETIC AGENTS

[75] Inventors: Otto Mauz, Liederbach, Taunus; Ernold Granzer, Kelkheim, Taunus, both of Germany

[73] Assignee: Hoechst Aktiengesellschaft, Frankfurt am Main, Germany

[22] Filed: Aug. 16, 1973

[21] Appl. No.: 389,004

[30] Foreign Application Priority Data
Aug. 18, 1972 Germany............................ 2240609

[52] U.S. Cl.................................. 424/308; 424/317
[51] Int. Cl.².......................................... A61K 31/235
[58] Field of Search............................ 424/317, 308

Primary Examiner—Jerome D. Goldberg
Assistant Examiner—Daren M. Stephens
Attorney, Agent, or Firm—Curtis, Morris & Safford

[57] ABSTRACT

Pharmaceutical compositions acting on the metabolism which contain as active derivatives of the 4-hydroxy-3,5-di-akylphenyl-propionic acid corresponding to the formula I and II

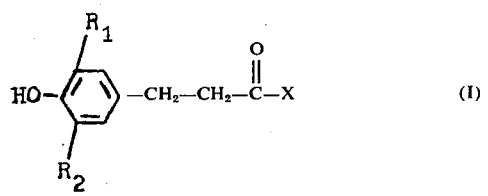

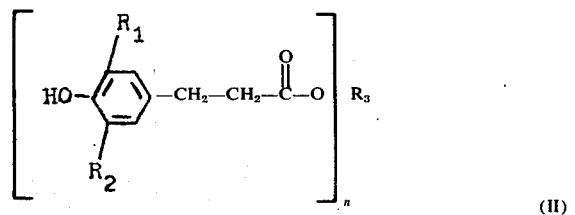

wherein
$R_1$ and $R_2$ which may be identical or different, each stands for an alkylradical having 1 to 8 carbon atoms,
$R_3$ stands for an alkylene radical having 2 to 12 carbon atoms,
X stands for hydroxy, alkoxy having 1 to 18 carbon atoms, phenalkoxy having 1 to 4 alkyl carbon atoms, cycloalkoxy having 5 to 8 carbon atoms, —$NR_4R_5$ in which $R_4$ stands for an alkyl group having 1 to 18 carbon atoms, $R_5$ stands for a hydrogen atom or $R_4$ and $R_5$ may form with the nitrogen atom a heterocyclic six-membered ring which may carry another hetero atom and $n$ is an integer from 2 to 4 and process for preparing them.

16 Claims, No Drawings

4-HYDROXY-3,5-DI-ALKYL-PHENYL-PROPIONIC ACID COMPOSITION SUITABLE AS LIPID LOWERING AND ANTI-DIABETIC AGENTS

The present invention relates to derivatives of the 4-hydroxy-3,5-di-alkyl-phenyl-propionic acid having an effect on the metabolism and corresponding to the formula I and II

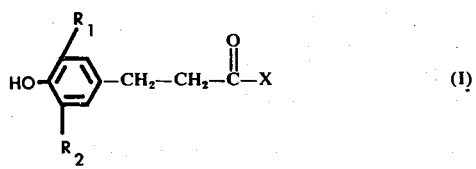

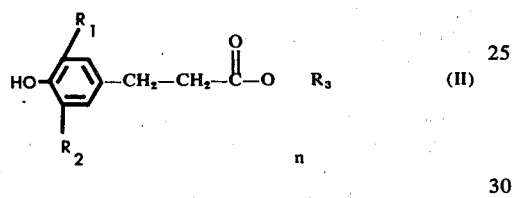

wherein
$R_1$ and $R_2$ which may be identical or different, each stands for an alkyl radical having 1 to 8 carbon atoms,
$R_3$ stands for an alkylene radical having 2 to 12 carbon atoms,
X stands for hydroxy, alkoxy having 1 to 18 carbon atoms, phenalkoxy having 1 to 4 alkyl carbon atoms, cycloalkoxy having 5 to 8 carbon atoms, $-NR_4R_5$ in which $R_4$ stands for an alkyl group having 1 to 18 carbon atoms, $R_5$ stands for a hydrogen atom or $R_4$ and $R_5$ may form with the nitrogen atom a heterocyclic six-membered ring which may carry another hetero atom and
n is an integer from 2 to 4.

The alkyl or alkoxy radical defined above or hereinafter is herein meant to be one having a linear or branched carbon chain.

Some of the 4-hydroxy-3,5-di-alkyl-phenyl-propionic acid derivatives coming within the formula I and II have been disclosed in the art (for example Coffield, J. Amer. Chem. Soc. 79 (1957), 5022, Robinson, J. Chem. Soc. 127 (1925), 1973, Papa, Schwenk and Whitman, J. Org. Chem. 7, (1942), 588, U.S. Pat. No. 3,644,482). Those compounds of formulae I and II which are known from the art have been disclosed to have utility as stabilizers for plastics, polymers, vegetable and animal oils.

Compounds of formula I in which X is a phenyl alkoxy radical having 1 to 4 alkyl carbon atoms or a $-NR_4R_5-$group in which $R_4$ and $R_5$ are defined as above have not yet been disclosed.

It has now been found that 4-hydroxy-3,5-di-alkyl-phenyl-propionic acid derivatives of the formulae I and II have a therapeutic action on the metabolism and can therefore be used as medicaments. Their hypolipemic and hypoglycemic activity and, hence, their utility, was surprising and not taught by the state of the art.

Objects of the invention are therefore 4-hydroxy-3,5-di-alkyl-phenyl-propionic acid derivatives of the formulae I and II which have a therapeutic effect on the metabolism, their preparation as well as pharmaceutical compositions containing them as active substance.

The substituents $R_1$ and $R_2$ preferably stand for identical alkyl radicals having 1 to 4 carbon atoms, especially t-butyl radicals.

In addition to the free acids of formula I there are especially considered esters with aliphatic, linear alcohols, phenyl-ethyl alcohol and benzyl alcohol. Among the amides, butyl and benzyl amides and morpholides are preferred.

$R_3$ stands for a linear or branched alkylene radical preferably having 2 to 6 carbon atoms.

The compounds of formulae I and II can be prepared according to known methods.

The processes comprise
a. reacting compounds of the general formula III

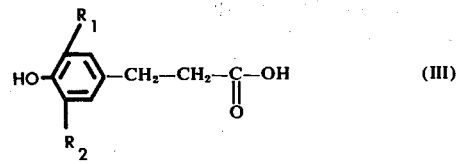

in which $R_1$ and $R_2$ are defined as above with corresponding monovalent to tetravalent alcohols to obtain the esters coming under formulae I and II b. reacting esters of the general formula IV

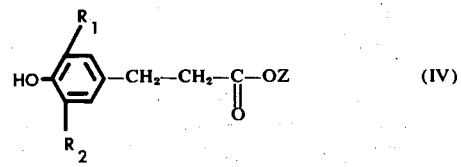

in which Z stands for any organic radical and $R_1$ and $R_2$ are defined as above, with compounds of the formula H-X in which X stands for hydroxy, alkoxy having 1 to 18 carbon atoms, phenalkoxy having 1 to 4 carbon atoms or cycloalkoxy having 5 to 8 carbon atoms, c. reacting compounds of the formula III with corresponding substituted amines to yield compounds of the formula V

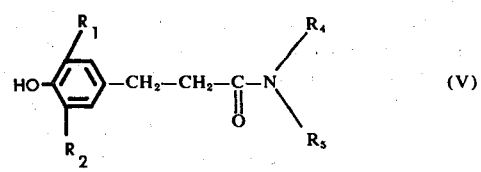

in which $R_1$, $R_2$, $R_4$ and $R_5$ are defined as above,
d. introducing into compounds of the formulae I and II in which $R_1$ and/or $R_2$ stands for hydrogen, one or several alkyl radicals having 1 to 8 carbon atoms,
e. saponifying nitriles of the formula VI

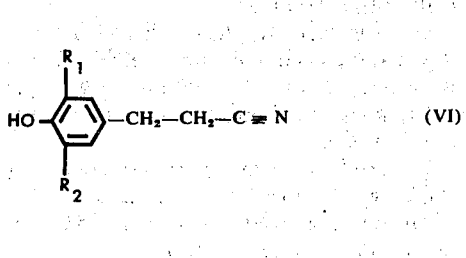

in which $R_1$ and $R_2$ each stands for alkyl radicals having 4 to 8 carbon atoms to yield the acids,
f. hydrogenating 4-hydroxy-3,5-di-alkyl-cinnamic acid of the general formula VII

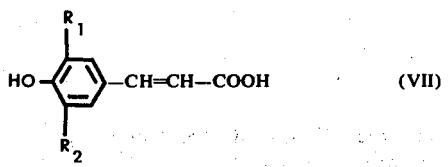

to yield the compounds of formula III,
g. reacting 2,6-dialkyl-phenols with acrylic acid esters of the formula $CH_2=CH_2-CO-O-Z$ in which Z stands for any organic radical in the presence of t-butylate and t-butyl-alcohol as solvents and optionally further working the reaction products according to method b) indicated above.

The acids of formula III which are used according to methods (a) and (c) can be obtained for example, according to methods (d), (e), (f) and (g).

The esterification (method a), preparation of the amides (method c) and the transesterification is carried out under the conditions known for that type of reactions, the starting compounds for methods (a) and (c) advantageously being active derivatives of the acids, for example, the acid chlorides of esters.

The esters of formula IV are obtained from the acids or the reactive acid derivatives according to known methods.

The compounds which are alkylated according to methods (d) may, for example, be obtained according to methods (a) to (c) and (e) to (g). The alkylation is preferably carried out with alkyl halides. The t-butyl radical is suitably introduced, for example, using isobutylene in the presence of Friedel-Crafts' catalysts.

The nitriles of formula VI, for example, the 4-hydroxy-3,5-di-t-butyl-phenyl-propionic acid nitrile are advantageously prepared by cyanoethylation of 2,6-di-t-butyl-phenol in the presence of a catalytical amount of 2,6-di-t-butyl-phenolate (cf. T. H. Coffield, J. Amer. Chem. Soc. 79 (1957), 5022). The nitrile obtained is then, for example, saponified with alcoholic potassium hydroxide solution.

The 4-hydroxy-3,5-di-alkyl-cinnamic acid according to process (f) can be hydrogenated according to various methods (cf. Robinson J. Chem. Soc. 127 (1925) 1973, Papa, Schwenk and Whitman, J. Org. Chem. 7 (1942), 588). Cinnamic acid derivatives of the formula VII are obtained, for example, from 4-hydroxy-3,5-di-t-butyl-benzaldehyde and malonic acid (ibid.). According to the indications made in Houben-Weyl, Methoden der organischen Chemie, vol. VII/1, page 25 or page 158 (1954). 4-hydroxy-3,5-di-t-butyl-benzaldehyde is obtained from 2,6-di-alkylphenol or by oxidation of 2,6-di-alkyl-4-methyl-phenol.

The 2,6-dialkyl-phenols are advantageously reacted with acrylic acid esters (method g) under the conditions disclosed in U.S. Pat. No. 3,644,482.

In addition to the compounds mentioned in the Examples the following compounds are preferred according to the invention:
4-hydroxy-3,5-dimethyl-phenyl-propionic acid
4-hydroxy-3,5-di-isopropyl-phenyl-propionic acid
4-hydroxy-3,5-di-t.-octyl-phenyl-propionic acid
4-hydroxy-3-methyl-5-t.-butyl-phenyl-propionic acid
4-hydroxy-3,5-di-t.-butyl-phenyl-propionic acid-n-dodecyl ester
bis(4-hydroxy-3,5-di-t.-butyl-phenyl-propionic acid)-glycol ester
bis(4-hydroxy-3,5-di-t.-butyl-phenyl-propionic acid)-butandiolester (1,4)
bis(4-hydroxy-3,5-di-t.-butyl-phenyl-propionic acid)-hexandiolester (1,6)
bis(4-hydroxy-3,5-di-t.-butyl-phenyl-propionic acid)-dodecandiolester (1,12)
tris(4-hydroxy-3,5-di-t.-butyl-phenyl-propionic acid)-glycerin ester
4-hydroxy-3,5-dimethyl-phenyl-propionic acid-phenyl ethyl ester
4-hydroxy-3,5-diisopropyl-phenyl-propionic acid-cyclohexyl ester
4-hydroxy-3,5-di-methyl-phenyl-propionic acid -butyl amide.

The compounds of formulae I and II have valuable therapeutical properties. They reduce serum lipid levels and may therefore be used for the therapy of primary hyperlipemiae and certain secondary hyperlipemiae which may, for example, occur in the case of diabetes, the most favourable effect on a disturbed diabetic metabolism being accompanied by a hypoglycemic activity of these compounds.

Since hyperlipemiae is the most dangerous cause of coronary heart disease and, generally speaking, elevated serum lipid values involve a great risk of causing arteriosclerotic diseases also of different localisation and not only of the coronary vessels, the reduction of elevated serum lipid levels is extremely important for the prevention and therapy of arteriosclerosis, especially of the coronary heart vessels. Being able to reduce normal and elevated serum lipid levels in animals, the abovespecified substances are useful for the treatment and prevention of human and animal arteriosclerotic diseases, especially of the coronary vessels but also of other blood vessels.

While having an extremely low toxicity (see $LD_{50}$ values in Table 1) the compounds of formulae I and II are capable of reducing the lipid level in the blood considerably. Their hypoglycemic activity could, inter alia, be demonstrated by the following animal tests:

1. *Male* rats having a *normal* serum lipid content were being treated for eight days with different daily doses mentioned in Table 1. The values given in that Table stand for a change in the serum concentrations of certain lipid classes.

The doses were administered per os by means of an esophagal sound. Generally, prior to and after the treatment, blood samples were taken and the concentration of cholesterol in the serum was determined according to the method of Lauber and Richterich and that of triglycerides according to the method of Eggstein and Kreutz. In the examples of the following Table 1, the changes in the serum lipid values due to the treatment with the substances of the invention are defined as follows:
   a. The changes in percent in the final value of the treated group, referred to the initial value of the treated group, the initial value being 100 per cent, and
   b. the change in the final value of the treated group, referred to the final value of an accompanying untreated control group, the untreated group's value being defined as 100%. Thus, the value given in columns A is the change in percentage referred to the initial value, the value given in columns B is the change in percentage of the treated group, referred to the untreated control group.

2. Dietetic-medicamentous hypercholesteremia of male rats

All the animals were fed with a diet food containing 2% of cholesterol, 2% of sodium cholate, 0.3% of methyl-thio-uracil, 20% of coco fat and 44% of cane sugar. The serum lipid concentration of the animals treated with the cited compounds was compared to that of an untreated control group being on the same diet which causes the serum cholesteral concentration to rise within one week to about 10 times the initial value, that of the serum triglycerides to 3 times and that of the phospholipids in the serum to 4 times the initial value. The lipid phosphorus was determined according to the method of Messrs. Boehringer Mannheim W. Germany. At the same time as the diet was offered the cited compounds were administered once a day to groups of rats, each containing 10 animals, over a period of 8 days by means of an esophagal sound. The change in percentage in the serum lipid concentration as compared to the control group (diet without active substance) is indicated in Table 2.

3. The hypertriglyceridemia induced by carbohydrates and initiated by fructose doses in male rats was substantially reduced by a three-day oral pretreatment with the cited substances in comparison to untreated control animals (Table 3).

TABLE 1

Reduction of serum lipid values in normolipemic rats
Change in percentage after oral administration of 8 doses to male rats in mg/kg/day

| | 100 | | | | 30 | | 10 | | | |
|---|---|---|---|---|---|---|---|---|---|---|
| Compound of Example | serum cholesterol A   B | | serum triglyceride A   B | | serum cholesterol A   B | | serum triglyceride A   B | | serum cholesterol A   B | serum triglyceride mg/kg | p.o. LD$_{50}$ male mice |
| 3 | | | −33/−16 | | | | /−25 | | | | 8000 |
| 7 | −5/−7 | | /−17 | | | | /−27 | | | | >8000 |
| 2 | /−12 | | −32/−38 | | | | −23/−38 | | | −21/−26 | |
| 5 | −3/ | | −60/−71 | | | | /−42 | | | /−3 | |
| 6 | −10/ | | −54/−58 | | | | /−27 | | | /−17 | |
| Clofibrat | | | | | −7/−7 | | +4/−13 | | | | 2000–2500 |

TABLE 2

Antihyperlipemic action on male rats after induction of a dietetic-medicamentous hyperlipemia starting with the first preparation administration.
Effect after administration of 8 doses

| | | Change in percentage referred to the untreated group by administering | | |
|---|---|---|---|---|
| Compound | mg/kg/day | serum triglycerides | serum cholesterol | phospholipids in the serum |
| Example 3 | 100 | −38 | −20 | −27 |
| Clofibrat | 100 | −27 | 0 | −12 |

TABLE 3

Change in percentage after administration of fructose and 3 doses per os on the male rate per mg/kg/day

| | 100 | | 30 | |
|---|---|---|---|---|
| Compound | Serum cholesterol | Serum triglycerides | Serum cholesterol | Serum triglycerides |
| Example 3 | | −35 | | |
| Example 7 | | −24 | | |
| Example 2 | −35 | −59 | | |
| Example 5 | | | | −50 |
| Example 6 | | | | −33 |
| | | | | −38 |

The favorable action of the compounds of formulae I and II on the dusturbed diabetic metabolism is not only based on a normalization of the disturbed lipid metabolism, i.e. on their hypolipemic activity, but also on an action on the carbohydrate metabolism.

The hypoglycemic activity had been established as follows, the blood sugar level having been determined by means of an autoanalyzer:

1. On alloxan-diabetic male rats substituted with insulin before the beginning of the test, that were offered food ad libitum, 100 mg/kg/day of 4-hydroxy-3,5-di-t.-butyl-phenylpropionic acid n-octadecyl ester administered per os once a day during 8 successive days lowered the blood sugar level 20 hours after the last administration by −18% as compared with an untreated group.

2. In the tolerance test with glucose doses administered per os to male rats that had fasted for 22 hours and that were administered 19 and 3 hours before the glucose administration (1g/kg) per os 100 mg/kg of the test preparation, 4-hydroxy-3,5-di-t.-butyl-phenyl-propionic acid n-octadecyl ester caused a lowering of the blood sugar level by −21% 3 hours after being fed with glucose. The lowering was in the same order of magnitude as that obtained with the comparison preparation phenformin.

In the case of male rats having been feed fructose doses per os and pretreated for 3 days with 100 mg/kg/day of the same compound, the blood sugar level was lowered by −17% 24 hours after the last administration.

Owing to their favorable effects on the lipid and carbohydrate metabolism, the compounds of formulae I and II are especially suitable as antidiabetics and hypolipemics.

The 4-hydroxy-3,5-di-alkyl-phenyl-propionic acid derivatives of formulae I and II may be administered as such or in admixture with pharmacologically acceptable carriers, an oral dosage unit form being preferred. For this purpose, the active substances are mixed with known excipients and brought into suitable dosage unit forms according to known methods, for example, into granules, tablets, hard gelatine capsules, emulsions, aqueous or oily suspensions or aqueous or oily solutions. As inert carriers and fillers, there may, for example, be mentioned diluents, such as magnesium carbonate, talcum or lactose; granulating and disintegrating agents, such as starch or alginic acid; binders, for example starch or geltin, and lubricants, such as stearic acid, talcum or magnesium stearate, for the preparation of dry compositions. The compositions may be obtained by dry or moist granulation and may be coated to retard disintegration or absorption in the gastro-intestinal tract, thus assuring a prolonged action. Suspensions, syrups or elixirs may also contain the active substance in admixture with usual excipients, for example, methyl cellulose, tragacanth or sodium alginate. As wetting agents, there may for example be mentioned lecithin or polyoxy-ethylene stearate. Oily carriers or solvents are especially vegetable or animal oils, for example peanut or sunflower oil or codliver oil. Moreover, the compositions may contain the usual additives, such as sweetening agents, flavoring agents, dyestuffs or preserving agents.

The daily dosage unit ranges from 0.5 to 4 g, preferably from 1 to 2 g, which is preferably administered in several portions each ranging from 0.2 to 1 g, preferably from 250 to 500 mg, two to four times per day.

A special utility of the novel compounds is that they can be combined with other active substances, for example with the following ones:

Antidiabetics, such as glycodiazine, tolbutamide, glibenclamide or agents acting on the circulatory system, especially those dilating the coronary vessels, such as chromonar or prenylamine and blood pressure lowering substances, such as Reserpin, $\alpha$-methyl-dopa or clonidine, further agents lowering the lipid level or geriatrics, psychopharmaceutics, for example, chlorodiazepoxide; diazepam, meprobamate or vitamins.

The following Examples serve to illustrate the invention.

EXAMPLE 1

4-hydroxy-3,5-di-t.-butyl-phenyl propionitrile 4 g of potassium were dissolved in 1 l of dry tert. butanol to which 51.5 g of 2,6-di-tert.-butyl-phenol (0.25 mol) were added while stirring. 21 g of acrylonitrile (0.5 mol) were added dropwise and the reaction mixture was heated under reflux for about 10 hours. After cooling the alcohol was separated by distillation in the vacuum. The residue was neutralized with dilute hydrochloric acid and then introduced in ether. The ether phase was washed several times with water, dried with sodium sulfate and the ether was extracted. The residue was recrystallized from heptane.

Melting point: 110°C
Analysis: $C_{17}H_{25}NO$.
Calculated: C, 78.70%; H, 9.72%.
Found: C, 78.96%; H, 9.62%.

EXAMPLE 2

4-hydroxy-3,5-di-t.-butyl-phenyl-propionic acid

A mixture of 259 g of 4-hydroxy-3,5di-t.-butylphenyl-propionitrile, 168 g of dry potassium hydroxide, 1 l of ethanol and 200 ml of water were heated under reflux for about 12 hours, it was cooled to 20°C and introduced into cold water. By adding hydrochloric acid the pH was adjusted at 4. The precipitate was suction-filtered and recrystallized from ethanol.

Melting point: 172°C
Analysis: $C_{17}H_{26}O_3$.
Calculated: C, 73.4%; H, 9.4%.
Found: C, 73.0%; H, 9.1%.

EXAMPLE 3

4-hydroxy-3,5-di-t.-butyl-phenyl-propionic acid-n-octadecyl ester 55 g of 4-hydroxy-3,5-di-t.-butyl-phenyl-propionic acid (0.2 mol) and 54 g of n-octadecyl alcohol (0.2 mol) were dissolved while hot in 600 ml of toluene and 50 g of a strongly acid ion exchanger (Amberlyst 15) were added. The water obtained through the esterification was separated by azeotropic distillation at the separator.

After separating the ion exchanger by filtration the toluene was removed under the water jet pump vacuum. The residue was recrystallized from methanol/ethyl acetate.

The 4-hydroxy-3,5-di-t.-butylphenyl-propionic acid-n-octadecyl ester was a white, crystalline powder having the melting point 50°C.

Analysis: $C_{35}H_{62}O_3$.

Calculated: C, 79.2%; H, 11.7%.
Found: C, 78.5%; H, 11.5%.

EXAMPLE 4

Bis-[4-hydroxy-3,5-di-t.-butylphenyl-propionic acid]-ethylene glycolester 278 g of 4-hydroxy-3,5-di-t.-butylphenyl-propionic acid (1 mol), 12 g of ethylene glycol (0.2 mol) and 100 g of strongly acid ion exchangers (Amberlyst 15) were suspended in 1 l of toluene and the reaction water was separated by azeotropic distillation over a water separator.

The toluene was withdrawn, the residue was absorbed in ether, shaken several times with sodium bicarbonate solution, and then washed with water. The ether phase was dried with sodium sulfate. After recrystallization from ethanol a crystalline product was obtained.

Melting point: 145°C.
Analysis: $C_{36}H_{54}O_6$.
Calculated: C, 74.18%; H, 9.33%.
Found: C, 73.6%; H, 9.1%.

EXAMPLE 5

4-hydroxy-3,5-di-t.-butylphenyl-propionic acid methyl ester 55 g of 4-hydroxy-3,5-di-t.-butylphenyl-propionic acid (0.2 mol) were dissolved in 500 ml of methanol and at 30°C dry hydrogen chloride was led in. The time of esterification was 40 hours.

Water was added to such an amount that the methyl ester was separated as a brown oil. The oily phase was separated and introduced into ether. The ether solution was washed with a saturated sodium bicarbonate solution and then several times with water. Drying was effected with sodium sulfate. After extracting the ether the residue was recrystallized from ethanol/$H_2O$.

Melting point: 65°C
Analysis: $C_{18}H_{28}O_3$.
Calculated: C, 74.0%; H, 9.58%.
Found: C, 73.8%; H, 9.7%.

EXAMPLE 6

4-hydroxy-3,5-di-t.-butylphenyl-propionic acid-n-butyl ester 28 g of 4-hydroxy-3,5-di-t.-butylphenyl-propionic acid (0.1 mol) were dissolved in 500 ml of butanol and saturated at 60°C for 48 hours with gaseous hydrogen chloride. The dissolved hydrochloric acid and the excess butanol were extracted by means of the water jet pump (20 mm mercury). The oily residue was dissolved at 146°C/0.3 mm mercury.

Analysis: $C_{21}H_{34}O_3$.
Calculated: C, 75.5%; H, 10.2%.
Found: C, 75.0%; H, 10.0%.

EXAMPLE 7

Tetra-(4-hydroxy-3,5-di-t.-butylphenyl-propionic acid)-pentaerythritol ester 13.6 g of pentaerythritol (0.1 mol) and 119 g of 4-hydroxy-3,5-di-t.-butylphenyl-propionic acid-methyl ester (0.41 mol) and 0.5 ml of titanium-tetra-butyl ester as catalyst were heated for about 10 hours to 190°C while nitrogen was led through, whereupon methanol was split off. The reaction mixture was taken up in benzene, it was separated by filtration while hot and the solvent was separated by distillation. The residue was treated with hexane to extract impurities if present. After eliminating the solvent the tetra-(4-hydroxy-3,5-di-t.-butylphenyl-propionic acid)-pentaerithritol ester was obtained as brittle resin.

Analysis: $C_{73}H_{108}O_{12}$.
Calculated: C, 74.4%; H, 9.2%.
Found: C, 73.8%; H, 9.6%.

EXAMPLE 8

4-hydroxy-3,5-di-t.-butylphenyl-propionic acid-cyclohexyl ester 27.8 g of 4-hydroxy-3,5-di-tert.-butylphenyl-propionic acid (0.1 mol) and 30 g of cyclohexanol (0.3 mol) were dissolved in 300 ml of toluene, 1 g of p-toluenesulfonic acid was added and the reaction water was separated by azeotropic distillation. Working up was effected in the manner described in Example 9.

32 g of a viscous substance remained as residue.
Analysis: $C_{23}H_{36}O_3$.
Calculated: C, 76.6%; H, 10.0%.
Found: C, 76.0%; H, 9.9%.

EXAMPLE 9

4-hydroxy-3,5-di-t.-butylphenyl-propionic acid-phenylethyl ester 27.8 g of 4-hydroxy-3,5-di-t.-butylphenyl-propionic acid (0.1 mol) and 36 g of phenylethyl alcohol (0.3 mol) were dissolved in 300 ml of toluene, 1 g of p-toluenesulfonic acid was added and the water obtained was separated by azeotropic distillation.

The toluene solution was shaken with saturated sodium bicarbonate solution, then several times with water; the toluene phase was separated and dried with sodium sulfate. The toluene was eliminated and the unreacted phenylethyl alcohol was separated by distillation at 70°C/1 mm mercury. 35 g of a slightly yellow coloured oil remained as residue.

Analysis: $C_{25}H_{34}O_3$.
Calculated: C, 78.4%; H, 8.9%.
Found: C, 78.0%; H, 8.8%.

EXAMPLE 10

4-hydroxy-3,5-di-t.-butylphenyl-propionic acid benzyl ester 27.8 g of 4-hydroxy-3,5-di-tert.-butylphenyl-propionic acid (0.1 mol) and 21.6 g of benzyl alcohol (0.2 mol) were dissolved in 300 ml of toluene, 1 g of p-toluenesulfonic acid was added and the water obtained was separated by azeotropic distillation. Working up was effected in an analogous manner to that of Example 9.

30 g of a solid glass-like substance remained as residue.
Analysis: $C_{24}H_{32}O_3$.
Calculated: C, 78.4%; H, 8.7%.
Found: C, 78.9%; H, 8.6%.

EXAMPLE 11

4-hydroxy-3,5-di-t.-butylphenyl-propionic acid-butyl amide 15.3 g of n-butyl amine (0.21 mol) were dissolved in 100 ml of heptane and at 20°C 29.6 g of 4-hydroxy-3,5-di-t.-butylphenyl-propionic acid chloride, dissolved in 200 ml of heptane, were added dropwise. After the addition completed the mixture was boiled under reflux for another 2 hours. The butylamine hydrochloride precipitated was suction-filtered while hot. When cooling 4-hydroxy-3,5-di-t.-butylphenyl-propionic acid butyl amide precipitated from the solution as crystals. After recrystallization from heptane 28 g of a white crystalline substance was obtained.

Melting point: 96°C.
Analysis: $C_{21}H_{35}NO_2$.
Calculated: C, 75.7%; H, 10.6%; N, 4.2%.
Found: C, 75.5%; H, 10.3%; N, 4.0%.

EXAMPLE 12

4-hydroxy-3,5-di-t.-butylphenyl-propionic acid morpholide 18.3 g of morpholine (0.21 mol) were dissolved in 100 ml of heptane; to that solution 29.6 g of 4-hydroxy-3,5-di-t.-butylphenyl-propionic acid-chloride (0.1 mol)-dissolved in 200 ml of heptane-were added dropwise at room temperature, whereafter it was boiled under reflux for another 2 hours. The morpholine hydrochloride precipitated was suction-filtered while hot and washed with hot heptane. When cooling the heptane solution 4-hydroxy-3,5-di-tert.-butylphenyl-propionic acid-morpholide precipitated as crystals. After recrystallizing again from heptane 30 g of a white crystalline substance was obtained.

Melting point: 132°C.
Analysis: $C_{21}H_{33}NO_3$.
Calculated: C, 72.6%; H, 9.5%; N, 4.0%. Found: C, 73.0%; H, 9.3%; N, 3.8%.

EXAMPLE 13

4-hydroxy-3,5-di-tert.-butylphenyl-propionic acid-benzyl amide

To a solution of 22.4 g of benzyl amine (0.21 mol) in 100 ml of heptane 29.6 g of 4-hydroxy-3,5-di-tert.-butylphenyl-propionic acid-chloride (0.1 mol) — dissolved in 200 ml of heptane — were added dropwise at 20°C, then the solution was boiled under reflux for 3 hours. Working up followed in the manner described in Example 12.

Yield: 25 g of white crystals having a melting point of 116°C.

Analysis: $C_{24}H_{33}NO_2$.
Calculated: C, 78.4%; H, 9.0%; N, 3.8%.
Found: C, 79.0%; H, 9.3%; N, 3.6%.

EXAMPLE 14

A compound as obtained according to Examples 1 to 13 was compressed into tablets such that each tablet contained 250 mg and could be administered orally as individual dosage unit.

EXAMPLE 15

A compound as obtained according to Examples 1 to 13 was mixed with lactose and the mixture was used to fill hard gelatin capsules of a suitable size at a mixing ratio of 250 mg of active substance to 100 mg of lactose per capsule.

EXAMPLE 16

A compound as obtained according to Examples 1 to 13 was compressed into tablets such that each tablet contained 500 mg of active substance.

EXAMPLE 17

A ground compound as obtained according to Examples 1 to 13 was mixed with lactose powder and ascorbic acid and the resulting mixture was used to fill hard gelatin capsules such that each capsule contained 500 mg of active substance, 200 mg of lactose and 20 mg of ascorbic acid.

EXAMPLE 18

100 g of a compound as obtained according to Examples 1 to 13, 20 g of calcium sulfate and 50 g of cane sugar were intimately mixed with each other and granulated with a hot 10% gelatin solution. The moist granules were screened through a U.S. standard sieve 16 mesh directly onto drying troughs. The granules were dried at 49°C and screened through a 20 mesh sieve. The dried granules were then blended with 30 g of starch, 10 g of talcum and 6 g of stearin and the mixture was screened through a U.S. standard sieve 60 mesh. Subsequently, it was compressed into tablets such that each tablet contained 250 mg of active substance.

EXAMPLE 19

250 mg of a compound as obtained according to Examples 1 to 13 were stirred with 750 mg of peanut oil to form a stiff paste which was used to fill soft gelatin capsules.

EXAMPLE 20

To make an orally administerable composition, 250 g of placebo granules consisting of 60% of lactose and 40% of starch were blended with 250 g of a compound as obtained according to Examples 1 to 13 and then 30 g of talcum and 20 g of magnesium stearate were added. The resulting mixture was compressed into tablets on a rotary tableting machine.

EXAMPLE 21

The following ingredients were blended with each other and compressed into tablets: A ground compound as obtained according to Examples 1 to 13 (250 mg), corn starch (140 mg), lactose powder (45 mg), talcum (30 mg), amylopectin (30 mg) and magnesium stearate (5 mg).

EXAMPLE 22

Linguettes were obtained by combining the following ingredients: An active compound as obtained according to Examples 1 to 13 (300 mg), magnesium stearate (15 mg), lactose (125 mg). These ingredients were thoroughly blended and used to fill hard gelatin capsules.

EXAMPLE 23

A mixture of 550 g of a compound as obtained according to Examples 1 to 13, 95 g of corn starch, 44 g of alginic acid and 3.6 g of magnesium stearate was molded into shaped structures which were then broken up into granules. The granules were screened through a U.S. standard sieve 8 mesh and blended with 3.4 g magnesium stearate. The resulting mixture was then compressed into tablets.

EXAMPLE 24

A mixture of 150 g of a compound as obtained according to Examples 1 to 13 and 44 g of corn oil was blended with 3.1 g of gum Arabic and 1.6 g of tragacanth. To this mixture, a solution of 0.1 g of a condensation product of cotyl alcohol and polyoxy-ethylene, 40 g of cane sugar, 0.025 g of propyl parahydroxy benzoate, 0.35 g of methyl parahydroxy benzoate and 108 g of water was slowly added. After a suitable flavoring agent and, where required, a suitable dyestuff had been added, the mixture was homogenized on a conventional device to form an emulsion suitable for oral administration. This emulsion was used to fill suitable containers.

EXAMPLE 25

110 g of a compound as obtained according to Examples 1 to 13 were ground together with a solution of 15 g of calcium cyclamate, 3 g of polyvinyl-pyrolidone, 1 g of methyl parahydroxy benzoate and 1.9 g of a condensation product of octyl cresol X 8 – 10 AEO in 100 ml of water in a ball mill for several hours to afford a suspension which was suitable for oral administration.

EXAMPLE 26

A mixture of some grams of sodium dioctyl sulfosuccinate dissolved in an adequate amount of methanol, 520 g of a compound as obtained according to Examples 1 to 13, 70 g of corn starch and 10 g of alginic acid was granulated, while admixing an adequate amount of an aqueous 10% corn starch paste. The granules were screened while stirring through a U.S. standard sieve 12 mesh and dried at 50° – 55°C. The dried granules were then screened through a U.S. standard sieve 12 mesh, 5 g of magnesium stearate were added and the mixture was compressed into tablets each containing 200 mg of active substance.

EXAMPLE 27

A mixture of 500 g of a compound as obtained according to Examples 1 to 13, 90 g of corn starch and 7 g of magnesium stearate was molded into shaped structures which were broken up into granules and screened through a sieve (8 mesh). The granules were then coated with an adequate amount of a mixture of 15 g of shellac, 3 g of olive oil and 800 g of ethyl alcohol. 3 g of magnesium stearate were added and the mixture was compressed into tablets each containing 250 mg of active substance.

We claim:

1. A pharmaceutical composition for lowering the lipid or blood sugar level comprising an effective amount for lowering the lipid or blood sugar level, in a unit dosage of 0.2 to 4 grams, of a 4-hydroxy-3,5-dialkyl-phenylpropionic acid or derivative thereof corresponding to formula I or II

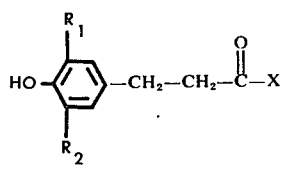

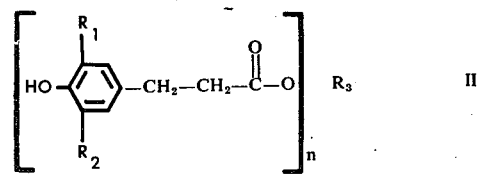

wherein:
$R_1$ and $R_2$, which may be identical or different, is alkyl of 1 to 8 carbon atoms, $R_3$ is alkylene of 2 to 12 carbon atoms, X is hydroxy, alkoxy of 1 to 18 carbon atoms, phenalkoxy of 1 to 4 alkyl carbon atoms or cycloalkoxy of 5 to 8 carbon atoms, and $n$ is an integer from 2 to 4, and a pharmacologically acceptable carrier therefor.

2. A pharmaceutical composition as claimed in claim 1, which comprises a content of 0.2 to 1 g of active substance.

3. A pharmaceutical composition as claimed in claim 1, which comprises 250 to 500 mg of active substance.

4. A pharmaceutical composition as claimed in claim 1, in the form of a capsule.

5. A composition as defined in claim 1 in which $R_1$ and $R_2$ are t.-butyl.

6. A composition as defined in claim 5 in which the active compound is 4-hydroxy-3,5-di-t.butylphenyl propionic acid.

7. A composition as defined in claim 5 in which the active compound is 4-hydroxy-3,5-di-t.butylphenyl acid-n-octadecyl ester.

8. A composition as defined in claim 5 in which the active compound is 4-hydroxy-3,5-di-t.butylphenyl propionic acid methyl ester.

9. A composition as defined in claim 5 in which the active compound is 4-hydroxy-3,5-di-t.butylphenyl propionic acid n-butyl ester.

10. A method of treatment for lowering the lipid or blood sugar level by oral administration which comprises administering to a patient a unit dosage of 0.2 to 4 grams of the active compound in a composition as defined in claim 1.

11. A method of treatment for lowering the lipid or blood sugar level by oral administration which comprises administering to a patient a unit dosage of 0.2 to 4 grams of the active compound in a composition as defined in claim 5.

12. A method of treatment for lowering the lipid or blood sugar level by oral administration which comprises administering to a patient a unit dosage of 0.2 to 4 grams of the active compound in a composition as defined in claim 6.

13. A method of treatment for lowering the lipid or blood sugar level by oral administration which comprises administering to a patient a unit dosage of 0.2 to 4 grams of the active compound in a composition as defined in claim 7.

14. A method of treatment for lowering the lipid or blood sugar level by oral administration which comprises administering to a patient a unit dosage of 0.2 to 4 grams of the active compound in a composition as defined in claim 8.

15. A method of treatment for lowering the lipid or blood sugar level by oral administration which comprises administering to a patient a unit dosage of 0.2 to 4 grams of the active compound in a composition as defined in claim 9.

16. The method of claim 10 for lowering the lipid or blood sugar level which comprises orally administering an effective amount of 0.2 to 1 gram per dosage unit of a 4-hydroxy-3,5-dialkylphenyl propionic acid or a derivative thereof as defined by formula I or II.

* * * * *